United States Patent [19]
Dykster et al.

[11] Patent Number: 5,712,893
[45] Date of Patent: Jan. 27, 1998

[54] REAL TIME RADIOGRAPHIC INSPECTION SYSTEM

[75] Inventors: Kerry R. Dykster, West Haven; Jeffery P. England, Clinton, both of Utah

[73] Assignee: Morton International, Inc., Chicago, Ill.

[21] Appl. No.: 743,866

[22] Filed: Nov. 5, 1996

[51] Int. Cl.$^6$ ................................................. G01B 15/06
[52] U.S. Cl. ............................................ 378/58; 378/205
[58] Field of Search ........................... 378/57, 58, 193, 378/176, 205

[56] References Cited

U.S. PATENT DOCUMENTS

| | | | |
|---|---|---|---|
| 5,467,379 | 11/1995 | Bybee et al. | 378/58 |
| 5,615,244 | 3/1997 | Dykster et al. | 378/57 |

*Primary Examiner*—Don Wong
*Attorney, Agent, or Firm*—Roger J. French; Gerald K. White

[57] ABSTRACT

A real time radiographic inspection system for inspecting a part includes a first, generally cylindrical housing having inner and outer substantially cylindrical coaxially aligned walls defining a substantially annular chamber therebetween. First and second through openings are formed in the outer cylindrical wall spaced substantially 180° apart. A through opening is formed in the inner wall aligned with the first through opening in the outer wall. A second housing extends radially outwardly from and surrounds the first through opening in the outer wall, while the second through opening in the outer wall defines an entrance to the annular chamber. An X-ray source is mounted in one of the first and second housings for directing an X-ray beam through the aligned through openings of the inner and outer walls. An image intensifier is mounted in the other of the first and second housings in alignment with the aligned through openings and positionable in registry with the X-ray beam. A rotating table is mounted in the first housing for rotating a part to be inspected through the chamber between the entrance opening and a position in registry with the X-ray beam.

20 Claims, 3 Drawing Sheets

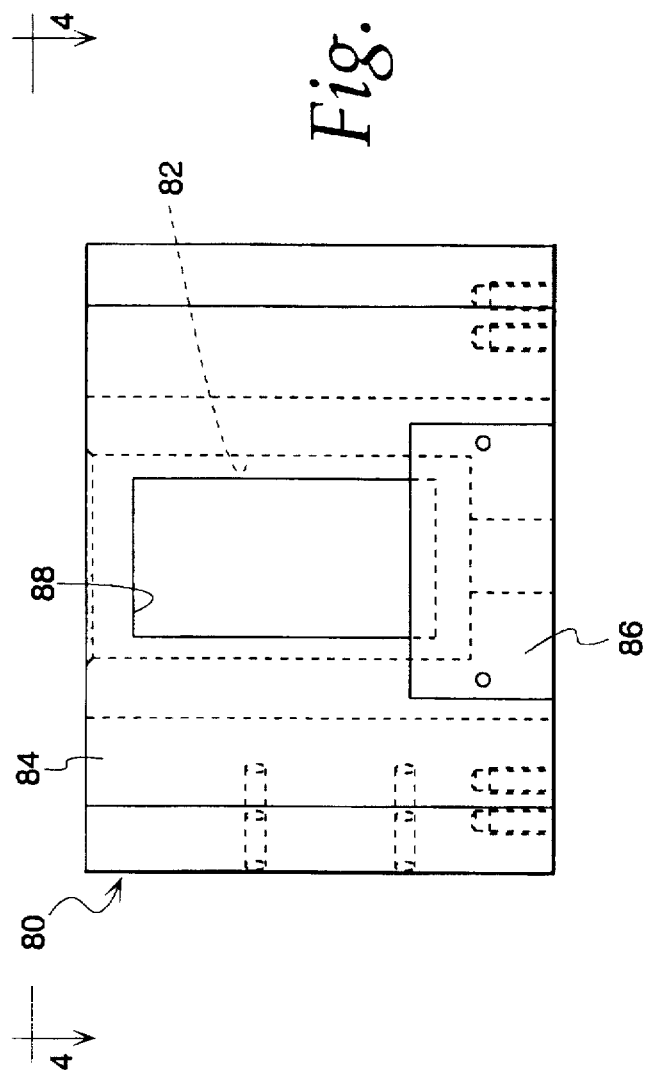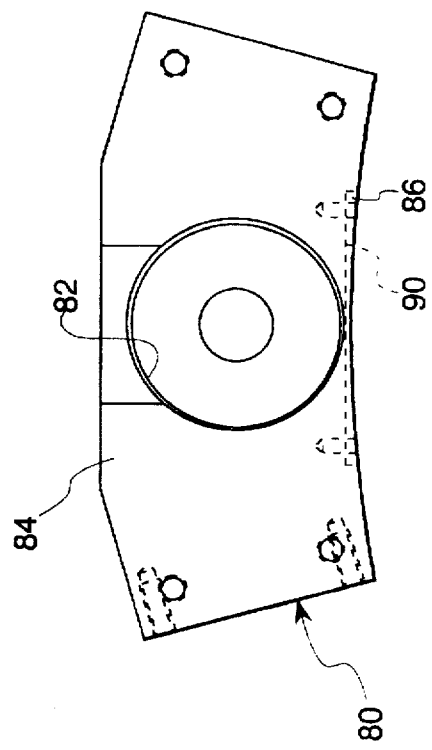

REAL TIME RADIOGRAPHIC INSPECTION SYSTEM

BACKGROUND OF THE INVENTION

The present invention is directed to a real time radiographic inspection system for testing articles such as production parts or assemblies. The invention is disclosed herein with specific reference to the use of such an inspection system for inspecting an inflator for an automotive vehicle airbag.

It is often desirable in the production process of various parts or assemblies to provide for real time testing or inspection of the part, assembly or subassembly at various stages of production prior to further processing. Elimination of unacceptable parts or assemblies at appropriate points in the production process is desirable. In order to maintain the efficiency of the process, it is desirable that such inspection or testing take place without appreciably slowing the production process.

In the case of real time radiographic (RTR) inspection, a number of benefits, but also a number of shortcomings, have been experienced with some prior art equipment and methods. In this regard, real time radiographic testing refers to the X-ray imaging in real time of articles, such as parts or assemblies, which are to be inspected. Criteria can be established for judging the acceptability or unacceptability of the images produced by such a system, such that unacceptable articles can be removed from the production process at an appropriate point. The use of data processing equipment in connection with such imaging permits the storage of data corresponding to such images and the records of previously tested articles for later verification, for recall purposes, or the like.

The use of X-ray imaging equipment requires the provision of an appropriate shielded enclosure or housing for the imaging equipment. This requirement makes it desirable that the articles which are to be tested be handled indirectly, e.g., by automated equipment, to accomplish individual X-ray imaging of the articles without physical entry of an operator into the shielded enclosure or housing. Some of the automated part handling systems employed in the prior art equipment have experienced a number of problems. Generally speaking, some of these systems were cumbersome, complicated in their design, and relatively slow in operation. These parts handling systems were often trouble-prone, due to their complexity, and difficult and time-consuming to repair. They were also relatively expensive to build, purchase and maintain. Thus, it is desirable that the article handling system be relatively simple, rugged and reliable and relatively easy to realign or repair.

Furthermore, it is desirable that the article handling equipment within the X-ray enclosure consistently handle and position each article relative to the X-ray beam to assure consistent imaging results for all tested articles. For the same reasons, it is desirable to maintain the proper geometry of the X-ray components to assure the consistent production of an acceptable and consistent image for each article. In this regard, it is also desirable to provide for relatively fast and simple adjustment of the alignment of the X-ray components. Preferably, in this regard, the X-ray equipment should be capable of real time, "X-ray on", image alignment. As a related matter, it is desirable that the X-ray components be relatively reliable and have low down time, being relatively easy to access for repair as necessary, so as to minimize interference with the production process.

As a still further matter, it is also desirable that the real time radiographic inspection system take up as little floor space as possible, because floor space is generally at a premium in production facilities.

Some of the prior art real time radiographic (RTR) systems for inspecting inflators have not provided many of the foregoing desirable features. For example, with respect to the article handling and positioning systems, some prior art real time radiographic test instruments mechanically present a product to the real time radiographic test instrument. In order to do this, these prior art systems would remove the product from the production line and introduce it into a separate X-ray enclosure. A number of sophisticated mechanical systems were provided to do this, such as sets of tooling to position the articles, an index table, a complex three-part gripping system and a complex product entrance and exit system with respect to the X-ray enclosure. The use of such complicated systems multiplies the number of areas in which malfunction can occur, resulting in disturbance of the production process; or can lead to misalignment or inconsistent handling of articles, resulting in inconsistent test results.

As indicated above, some of the prior art RTR inflator inspection systems have provided relatively cumbersome and complex internal article handling components and arrangements in which it has been difficult to maintain consistent alignment for consistent imaging by the X-ray beam. Real time, "X-ray on" image alignment was not possible. Some of these prior art systems have utilized relatively complex servo-motor alignment components, which never quite achieve the same positioning of an article relative to the X-ray beam from one article to another. Moreover, both the handling and X-ray imaging parts of these prior art systems had generally been designed such that they are relatively difficult to access, and difficult to adjust, realign or repair, requiring excessive down time in the production cycle to accomplish such adjustment, realignment or repair.

With respect to the enclosures or housings of prior art machines, these were generally designed around the relatively complex handling systems discussed above. This equipment usually required relatively large cabinets, thereby taking up large amounts of factory floor space.

OBJECTS AND SUMMARY OF THE INVENTION

Accordingly, it is a general object of the present invention to provide a real time radiographic inspection system which provides the above-discussed desirable features and overcomes the above-discussed shortcomings of some of the prior art systems.

Briefly, and in accordance with the foregoing objects, the present invention provides an improved real time radiographic test instrument comprising a first, generally cylindrical housing having inner and outer substantially cylindrical coaxially aligned walls defining a substantially annular chamber therebetween, and means defining respective opposite end closures for said annular chamber; means defining two through openings in said outer cylindrical wall spaced substantially 180° apart; means defining a through opening in said inner wall aligned with one of the two through openings in said outer wall; a second housing extending radially outwardly from and surrounding said one of said through openings in said outer wall; the other of said second through openings in said outer wall defining an entrance to said annular chamber; an X-ray source mounted in one of said first and second housings for directing an X-ray beam through the aligned through openings of said inner and outer walls; an image intensifier mounted in the other of said first and second housings in alignment with said aligned through openings and positionable in registry with said X-ray beam; and rotating means mounted in said first housing for rotating a part to be inspected through said chamber between said entrance opening and a position in registry with said X-ray beam.

BRIEF DESCRIPTION OF THE DRAWINGS

The features of the present invention which are believed to be novel are set forth with particularity in the appended claims. The organization and manner of operation of the invention, together with further objects and advantages thereof may best be understood by reference to the following description, taken in connection with the accompanying drawings in which like reference numerals identify like elements, and in which:

FIG. 3 is an elevation of a part carrier for use in the inspection system of FIGS. 1 and 2; and FIG. 4 is an end view of the part carrier of FIG. 3.

DETAILED DESCRIPTION OF THE ILLUSTRATED EMBODIMENT

Figure 1:
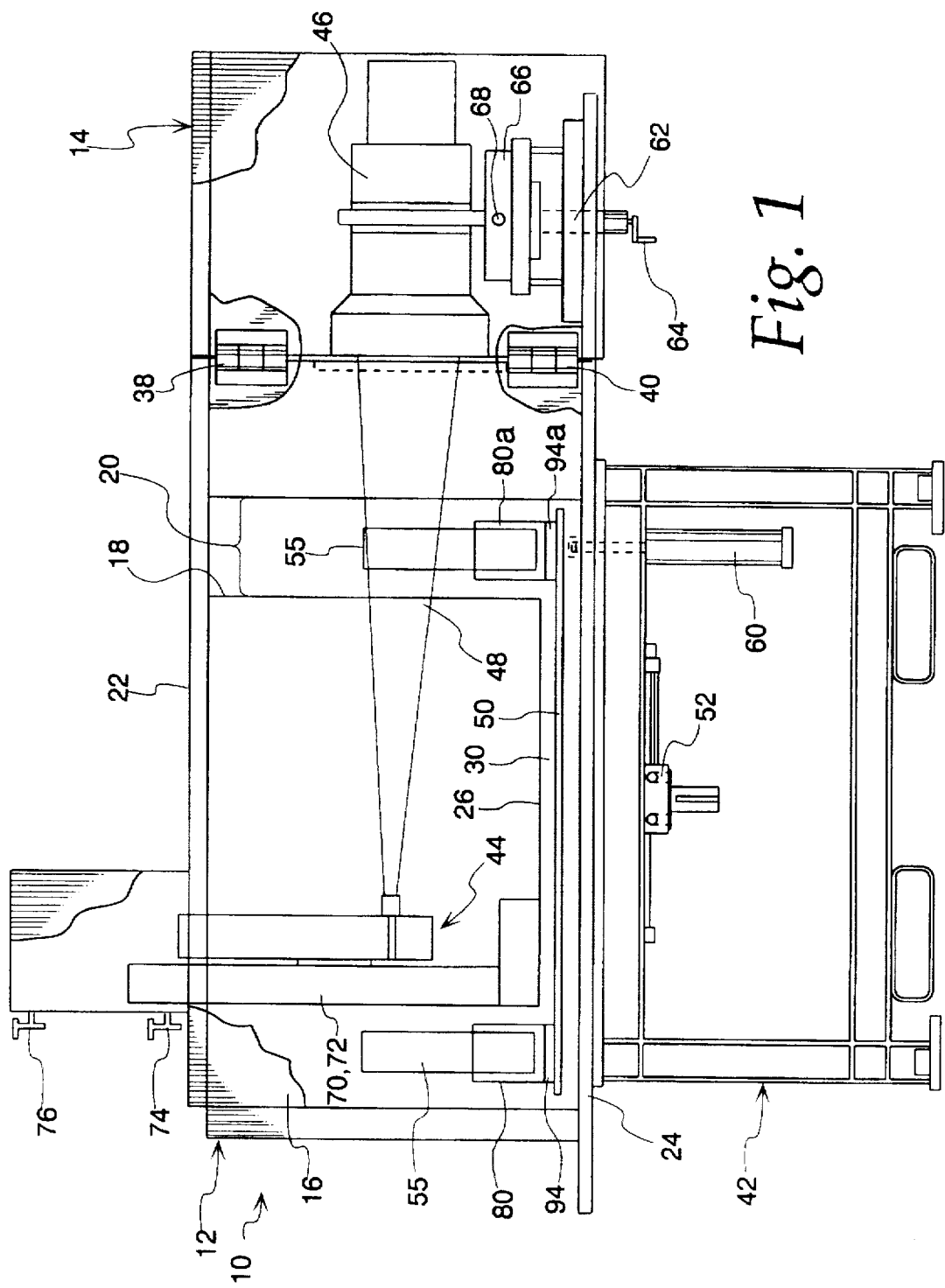
FIG. 1 is a side elevation, partially broken away, illustrating an improved real time radiographic inspection system in accordance with the invention.
Figure 2:
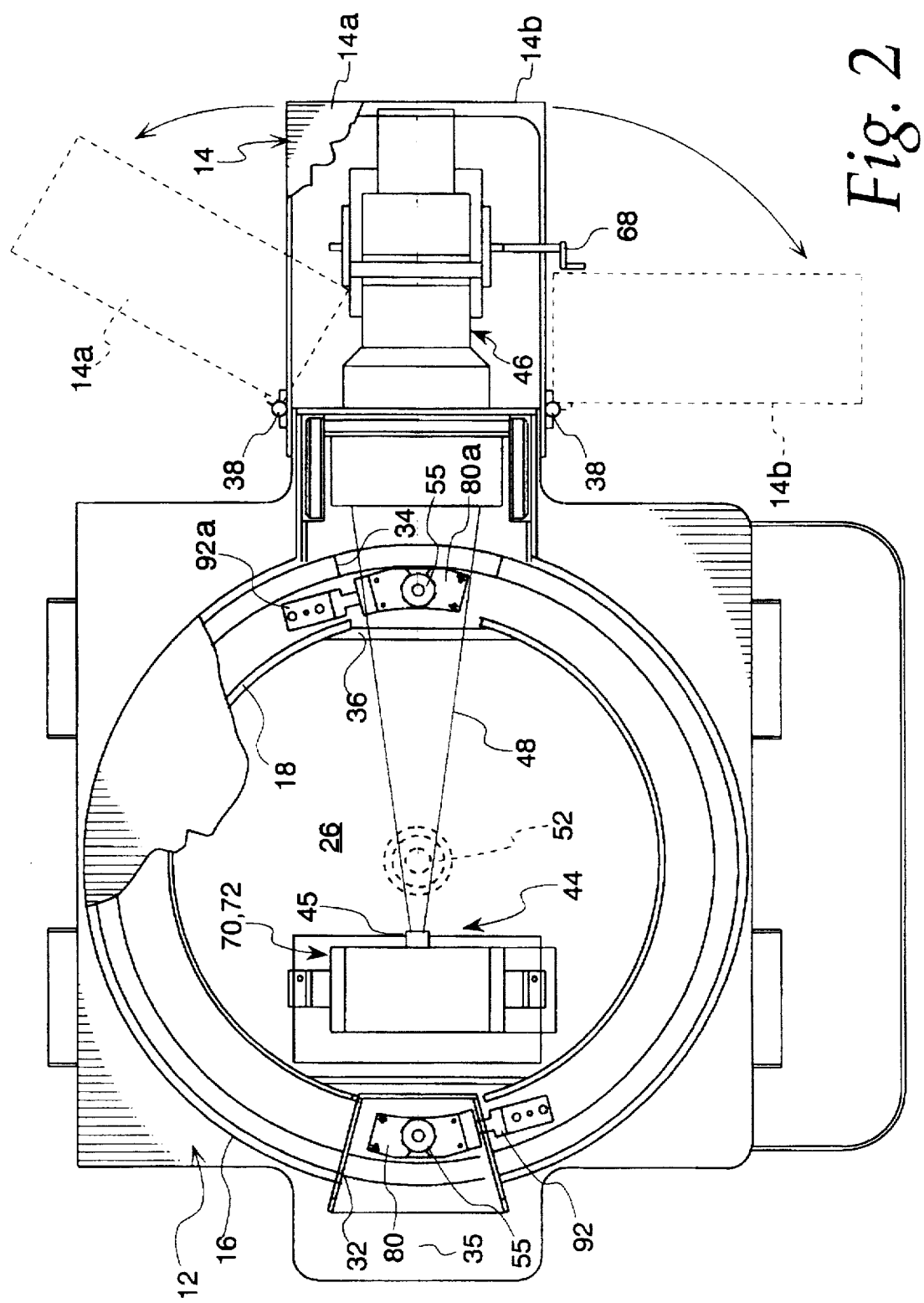
FIG. 2 is a top plan view, partially broken away, of the system of FIG. 1.

Referring now to the drawings, and initially to FIGS. 1 and 2, there is illustrated a real time radiographic inspection system in accordance with the invention, which is designated generally by the reference numeral 10. The system 10 is generally housed within a first housing or enclosure 12 and a second housing or enclosure 14 which are interconnected, as will be more fully described hereinbelow.

The first housing 12 is generally cylindrical in form and has a cylindrical outer wall 16 and a cylindrical inner wall 18 which is of smaller diameter than the outer wall 16 and is coaxially aligned therewith. Accordingly, a generally annular space or chamber 20 is defined between the outer and inner walls 16, 18. A top wall or panel 22 generally defines an upper end closure for the annular chamber 20. Similarly, a generally circular bottom wall or panel 24 forms a lower end closure. However, an inner circular wall 26 is also provided at an end of the inner cylindrical wall 18 opposite its end which is closed by the outer wall 22. This inner wall 26 is spaced somewhat above the lower closure or wall 24 to form a relatively short generally cylindrical space 30 therebetween, which communicates with the annular chamber 20. As best viewed in FIG. 2, the cylindrical outer wall 16 has an entrance opening 32 which communicates with the chamber 20.

In the illustrated embodiment the walls 16, 18, 22, 24 and 26 are constructed of a layered or laminated material consisting of a lead sheet sandwiched between two layers of steel.

A pair of aligned through openings 34, 36 are provided in the outer wall 16 and the inner wall 18 in an area substantially 180° apart from, and preferably centered about a common diameter 35 with the opening 32. The second through openings 34 and 36 are radially aligned with each other.

The second housing 14 extends generally radially outwardly from the opening 34 in the outer wall 16, and generally surrounds and encloses this opening 34. This second enclosure 14 is generally rectilinear in form, and has two halves 14a, 14b which are preferably hingedly joined in clam shell-like fashion to the first enclosure, for example by pairs of hinges 38, 40 which are located along respective sides thereof. Thus, access to the interior of the enclosure 14 may be had by releasing a suitable latch or other mechanism (not shown) at its midline and hingedly rotating or pivoting the two enclosure or housing halves 14a, 14b about these hinges 38, 40.

The respective housings 12 and 14, as best viewed in FIG. 1, are preferably mounted on a raised platform or support table 42. These two housings 12 and 14 house or enclose the components of a real time radiographic inspection or X-ray apparatus which includes, generally speaking, an X-ray source 44 and an image intensifier 46. While the X-ray source 44 and image intensifier 46 may be respectively mounted in either of the two enclosures 12 and 14, in the illustrated embodiment, the X-ray source 44 is mounted in the first housing 12, while the image intensifier 46 is mounted or located within the second housing 14.

More specifically, the X-ray source 44 is mounted and located in the housing 16 in such a way as to direct an X-ray beam 48 in the direction of and through the respective openings 34, 36 in the inner and outer walls 18 and 16 of the housing 12, and thus into the interior of the housing 14, which it will be remembered is joined with the housing 12 so as to substantially enclose and extend radially outwardly from the opening 34 in the outer wall 16. Accordingly, the image intensifier 46 is mounted and aligned in such a manner within the second housing 14 as to be in alignment or in registry with the X-ray beam 48.

Referring again to the generally cylindrical space 30 which intersects with and joins the annular chamber 20, there is mounted therein a generally circular rotating table 50 which is positioned for rotating a part or other article 55 to be inspected between a position wherein the part is introduced into the chamber 20 at the opening 32 to a position substantially 180° away, and in alignment with the openings 36 and 34, such that the article 55 to be inspected is in registry with the X-ray beam 48. In order to rotate the table 50 in this fashion, there is provided a rotary actuator assembly 52, which preferably includes an air\oil tandem rotary actuator made by PHD and designated as catalog number R23R-8180-D-A-E-G. However, other equivalent rotary actuator components may be utilized without departing from the invention.

We have found that the described configuration of the housings 12, 14 and of the cheer 20, as illustrated and described, prevents the escape of any significant measurable X-ray energy at the entrance opening 32. Therefore, this design permits operation without an X-ray primary safety interlock, which was required with most prior art designs. Moreover, this configuration permits use of a relatively simple handling system, as described above, for moving the article between the entrance opening 32 and a position in registry with the X-ray beam 48.

Without limiting the invention in any way, but for purposes of giving a specific example, the X-ray source tube 44 may be a Comet Model MXR160 X-ray source tube. The image intensifier 50 may be a 9-inch single model with direct coupled CCD camera, available for example from North American Imaging, Camarillo, Calif. The X-ray source tube is also preferably provided with a beam blocker (not shown) which can be rotated in and out of registry with the X-ray beam 48 by a rotary actuator (not shown), such as a rotary actuator part no. XR071-0907L-RB23M available from Parker-Hannifin Corp. of Wadsworth, Ohio.

In the illustrated embodiment, there is also provided a lift means or assembly 60 which is positioned for lifting or elevating and lowering an article 55 which is in registry with the X-ray beam 48. Thus, the lift assembly 60 is located generally beneath the chamber 20 and generally centered on the same diameter 35 below the center lines of the respective openings 34 and 36 in the outer and inner walls 16 and 18 of the housing or enclosure 12. In the illustrated embodiment, the lift mechanism employs an air cylinder made by SMC and designated as part number NCDA1KF250-0850; however, other equivalent parts or assemblies may be utilized without departing from the invention.

In the illustrated embodiment, the article or part 55 to be inspected is an elongated cylindrical inflator assembly, and it is desired to obtain a real time radiographic image at two locations along the longitudinal axis thereof. However, it will be understood that in the case of the inspection of other articles or parts of different configurations, such multiple radiographic inspections or analyses may or may not be desired, whereby the lift mechanism or assembly 60 might be eliminated or modified as appropriate to the specific imaging task to be accomplished while the part 55 is in the portion of the chamber 20 where it may be placed in registry with or in alignment with the X-ray beam 48.

Referring to the image intensifier 46 within the housing or enclosure 14, in the illustrated embodiment, additional adjusting means are provided for selectively varying the position of the image intensifier 46 relative to the X-ray beam 48 to achieve real time X-ray on image alignment. In the illustrated embodiment, these adjusting means comprise a first or vertical (up/down) position adjusting means designated generally by the reference numeral 62, which has a control member 64 projecting externally of the housing 14. The arrangement is such that the vertical position or height of the image intensifier 46 may be adjusted from outside of the housings 14 and 12. Similarly, a horizontal image intensifier position adjustment is designated generally at reference numeral 66, and has an externally projecting adjustment member 68, whereby the horizontal (left/right) position of the image intensifier may also be adjusted relative to the X-ray beam 48 from outside of the housings 12 and 14. The position adjusting means for adjusting the horizontal and vertical positions of the image intensifier may comprise a Milwaukee slide, model no. R-6686, available from Milwaukee Slide, Milwaukee, Wis.

Similarly, and referring to the X-ray source 44, a source tube 45 may be adjusted in both vertical and horizontal directions to achieve repositioning or adjustment of the X-ray beam 48 to achieve real time X-ray on image alignment. In similar fashion to the image intensifier as described above, respective horizontal and vertical source adjustments are indicated diagrammatically at reference numeral 70 and 72 and have externally projecting adjustment members 74 and 76. This arrangement is such that the position of the X-ray beam 48 produced by the X-ray source tube 45 may be adjusted along three axes from outside of the housing 12 while the X-ray beam is on, that is, for achieving real time X-ray on image alignment, as mentioned above. The position of the X-ray source tube 45 may be adjusted by use of a two axis EC series positioning stage having X-travel (left/right) of 6 in., y-travel (up/down) of 12 in. and a lead screw having 0.200 lead, available from DCI, Franklin, Mass.

Referring also to FIGS. 3 and 4, in the illustrated embodiment, a carrier member or assembly 80 is preferably utilized to hold the article 55 to be inspected in position on the rotary table 50. In the illustrated embodiment, two identical such carrier assemblies 80 and 80a are provided, located substantially 180° apart on the table 50. Thus, a previously inspected article may be removed from the carrier 80, which in the drawings is shown in registry with the entrance opening, while a second article or part located in the carrier 80a is being subjected to a real time radiographic inspection in registry with the X-ray beam 48.

As shown in FIGS. 3 and 4, a carrier 80 is generally arcuately shaped so as to readily fit within the generally annular chamber and upon the rotary table 50 for rotation within the annular chamber 20. The carrier 80 includes a chamber or nest portion 82, which is internally shaped complimentary with the shape of the article to be inspected, and in the illustrated embodiment is generally an elongate cylindrical space for receiving a portion of the elongate cylindrical inflator 55. Preferably, the nest portion 82 is formed in a body or block 84 of plastics material which is substantially transparent to the X-ray beam 48 such that the part or article, or at least a portion thereof held within the nest 82, may be readily inspected by the X-ray inspection apparatus of the invention. Also, the block 84 has a rectangular opening or window 88 which opens onto the nest 82 to further enhance the X-ray image of the inflator 55 to be carried in the nest.

The block 84 mounts to a slide assembly 92 (see FIG. 2), which guides the up-down motion of the block in response to the lift mechanism 60. Also, a metal plate 94 (see FIG. 1) mounts to the bottom of the block to provide a firm surface for the lift mechanism 60 to bear against.

In the illustrated embodiment, a filter in the form of a small plate of X-ray diffracting metallic material (e.g. copper), indicated here by reference numeral 86, is provided mounted to a recess 90 in the surface of the plastic block 84 in which the nest 82 is formed in order to form a filter to cause the X-ray beam to impinge upon predetermined portions of the article to be inspected. In the embodiment illustrated, the recess 90, and hence the plate 86, overlap a small part of the window 88. The number and position of such filters will depend upon the specific article to be tested. Similarly, it should be understood that the specific shape of the nest 82 formed in the block 84 may vary from what is shown in order to accommodate articles of different configurations. The elongated cylindrical inflator 55 is shown in FIGS. 1 and 2 for purposes of illustration.

In operation, a part 55 to be inspected, such as the hybrid inflator, may be introduced into the nest 82 in the carrier 80 through the entrance opening 32. This may be done either manually or by the use of a suitable automated parts handling apparatus (not shown). Thereupon, the table 50 is rotated by the rotary actuator 52 substantially 180° in order to place the part or inflator 55 in registry with the X-ray beam 48. At this time, the second carrier 80a will be in registry with the entrance opening 32, whereby a second part such as an inflator to be inspected may also be placed in this second carrier 80a while the real time radiographic inspection of the first part is progressing.

In the illustrated embodiment, the lift mechanism or assembly 60 is utilized during the real time radiographic inspection to lift and/or lower the part 65 relative to the X-ray beam 48 in order to produce multiple images over multiple areas of the part, if desired. The carrier is provided with an external opening 88 which intersects the nest 86 to permit the lift mechanism to enter and lift the inflator 55. However, this lift assembly or mechanism need not be used in the case of parts whose shape or size is such that they may be inspected with a single imaging process by the X-ray apparatus.

During the real time X-ray-on inspection process, the relative positions of the X-ray beam 48 and of the image intensifier 46 may be adjusted if desired by use of the external adjustment members 64, 68 with respect to image intensifier 46 and external adjustment numbers 74, 76 78 with respect to the X-ray source tube 45. It should be understood that these adjustment numbers 64, 68 and 74, 76 78 may be adjusted either manually or by further automated apparatus such as motors (not shown), or the like, or by remote control (now shown) without departing from the invention. Upon completion of a real time radiographic test or test sequence upon a first part or inflator, the table 50 may again be rotated through 180° to return the just inspected part to the entrance opening 32 and to place the next part to be inspected in registry with the X-ray beam 48.

While particular embodiments of the invention have been shown and described in detail, it will be obvious to those skilled in the art that changes and modifications of the present invention, in its various aspects, may be made without departing from the invention in its broader aspect, some of which changes and modifications being matters of routine engineering or design, and others being apparent only after study. As such, the scope of the invention should not be limited by the particular embodiments and specific constructions described herein but should be defined by the appended claims and equivalents thereof. Accordingly, the aim in the appended claims is to cover all such changes and modifications as fall within the true spirit and scope of the invention.

The invention is claimed as follows:

1. A real time radiographic inspection system for inspecting an article, comprising: a first, generally cylindrical housing having inner and outer substantially cylindrical coaxially aligned walls defining a substantially annular chamber therebetween, and means defining respective opposite end closures for said annular chamber; means defining a pair of through openings in said outer cylindrical wall spaced substantially 180° apart; means defining a through opening in said inner wall aligned with one of the pair through openings in said outer wall; a second housing extending radially outwardly from and surrounding said one through opening in said outer wall; the other of said pair of through openings in said outer wall defining an entrance to said annular chamber; an X-ray source mounted in one of said first and second housings for directing an X-ray beam through the aligned through openings of said inner and outer walls; an image intensifier mounted in the other of said first and second housings in alignment with aligned through openings and positionable in registry with X-ray beam; and rotating means mounted in said first housing for rotating a part to be inspected through said chamber between said entrance opening and a position in registry with said X-ray beam.

2. Apparatus according to claim 1 wherein said inner and outer walls are respectively provided with spaced apart circular end surfaces at one end thereof defining a substantially cylindrical space therebetween intersecting said annular chanter, said end surface of said outer cylindrical wall defining one of said end closures of said annular chamber, and wherein said rotating means comprises rotary table means being mounted within said cylindrical space.

3. Apparatus according to claim 1 and further including adjusting means for selectively varying the position of said X-ray beam from outside of said first and second housings to achieve real time X-ray on image alignment.

4. Apparatus according to claim 1 and further including adjusting means for selectively varying the position of said image intensifier relative to said X-ray beam from outside of said first and second housings to achieve real time X-ray on image alignment.

5. Apparatus according to claim 3 wherein said adjusting means includes means for adjusting the position of said X-ray beam in two orthogonal directions.

6. Apparatus according to claim 4 wherein said adjusting means includes means for adjusting the position of said image intensifier in two orthogonal directions.

7. Apparatus according to claim 3 and further including adjusting means for selectively varying the position of said image intensifier relative to said X-ray beam from outside of said first and second housings to achieve real time X-ray on image alignment.

8. Apparatus according to claim 1 wherein said rotating means includes rotary table means and rotary actuator means for rotating said rotary table means.

9. Apparatus according to claim 1 and further including carrier means mounted to said rotating means and configured for securely holding a part to be inspected.

10. Apparatus according to claim 8 and further including carrier means mounted to said rotary table means and configured for securely holding a part to be inspected.

11. Apparatus according to claim 10 and further including second carrier means configured for securely holding a part to be inspected and mounted to said rotary table means substantially 180° away from the first carrier means.

12. Apparatus according to claim 10 wherein said carrier means includes filter means for causing the X-ray beam to impinge on predetermined portions of the part to be inspected.

13. Apparatus according to claim 12 wherein said filter means comprises at least one area of X-ray shielding material located on said carrier in a preselected position.

14. Apparatus according to claim 1 and further including lift means located in said chamber adjacent said first through opening for lifting said part in an axial direction in registry with said X-ray beam.

15. Apparatus according to claim 9 and further including lift means located in said chamber adjacent to said second through opening and wherein said carrier means includes an opening for permitting said lift means to engage a part to be inspected in an axial direction.

16. Apparatus according to claim 1 and further including hinged attachment means for hingedly connecting said second housing to said first housing.

17. A carrier apparatus for use with a real time radiographic inspection system having a generally annular chamber through which an article to be inspected is carried, said carrier apparatus comprising: a body portion defining a chamber of complementary configuration for receiving an article to be inspected and an external configuration of complementary form for interfitting within said annular chamber of said real time radiographic inspection system.

18. Apparatus according to claim 17 and further including a quantity of X-ray shielding material located on said body portion in a preselected position.

19. Apparatus according to claim 17 and further including at least one opening in said body portion communicating with said chamber and configured for permitting entry of article engaging means for engagement with an article carried in said chamber.

20. Apparatus according to claim 17 wherein said carrier means has a generally arcuate exterior configuration, complementary with an internal configuration of said annular chamber of said real time radiographic inspection system.

* * * * *